United States Patent
Lytle et al.

(10) Patent No.: US 6,199,696 B1
(45) Date of Patent: Mar. 13, 2001

(54) SHOCK RESISTANT PACKAGING FOR A PROSTHETIC HEART VALVE

(75) Inventors: Thomas W. Lytle, Round Rock; Tammi E. Klostermeyer, Austin, both of TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/320,029

(22) Filed: May 26, 1999

(51) Int. Cl.[7] .............................. A61B 17/06; B65D 85/30
(52) U.S. Cl. .............................. 206/438; 206/363; 53/409
(58) Field of Search .................................. 206/438, 363, 206/570, 583; 623/2, 900; 53/409, 467, 468, 473

(56) References Cited

U.S. PATENT DOCUMENTS

| 4,101,031 | 7/1978 | Cromie . | |
|---|---|---|---|
| 4,211,325 | * 7/1980 | Wright | 206/438 |
| 4,697,703 | * 10/1987 | Will | 206/438 |
| 4,801,015 | 1/1989 | Lubock et al. . | |
| 5,554,186 | * 9/1996 | Guo et al. | 623/2 |
| 5,560,487 | * 10/1996 | Starr | 206/438 |
| 5,720,391 | 2/1998 | Dohm et al. . | |
| 5,823,342 | 10/1998 | Caudillo et al. . | |

* cited by examiner

Primary Examiner—Luan K. Bui
(74) Attorney, Agent, or Firm—Timothy L. Scott; Philip S. Lyren

(57) ABSTRACT

A packaging container for a heart valve includes a container having a first inner barrier member and a second inner barrier member. A support shelf is mounted in the first inner barrier member of the container. A heart valve has a first side and a second side, first side being engaged with the support shelf. An insert member is engaged with the second side of the heart valve and is engaged with the second inner barrier member the packaging container is mounted within an outer barrier container.

11 Claims, 4 Drawing Sheets

SHOCK RESISTANT PACKAGING FOR A PROSTHETIC HEART VALVE

BACKGROUND

The disclosures herein relate generally to prosthetic heart valves and more particularly to a shock resistant package for a universal mechanical valve.

Present packaging for a universal mechanical valve includes an inner top barrier member and an inner bottom barrier member for housing the valve. The inner unit is steam sterilized and placed in an outer barrier member also including a top and bottom portion. The valve includes a pyrolite orifice having pyrolitic carbon leaflets. This arrangement permits shock loads to be transmitted directly to the valve components, i.e. orifice and leaflets, during shipping thus increasing the potential for shock induced damage. The purpose of the inner barrier device is to package the valve to be used for either an aortic or mitral orientation, i.e. inverted positions.

Examples of present packaging devices include U.S. Pat. No. 4,101,031 which discloses a package for a prosthetic heart valve or the like comprising a pair of separable mating package sections for receiving the heart valve and retaining it in a sterile manner in a biased position against a resilient pad. A separate retainer member is positioned in the package for biasing the heart valve against the pad, the retainer member being a rigid sheet having an aperture adapted to receive a portion of the valve. One of the mating package sections is provided with a shoulder which urges the retainer member into a biased position against the heart valve so that the valve is in turn biased against the resilient pad. The shoulder is adapted to slide along the surface of the retainer member so that torque is not transmitted to the heart valve when the package sections are rotated to open or close the package.

U.S. Pat. No. 4,801,015 discloses a device for releasably holding an object, particularly a prosthetic heart valve, comprising a handle member integral with a key member which releasably engages a holder member having an interacting engaging screw which controls and limits the movement of integral cooperating fingers for holding and releasing the object. A package assembly is provided for storing, under sterile conditions, a holder member of the device attached to a prosthetic heart valve comprising a clam shell mechanism for releasably holding the holder member and valve.

In U.S. Pat. No. 5,720,391, packaging and a holder are provided for a heart valve prosthesis. The holder is adapted to grasp the heart valve prosthesis and includes a post. The packaging includes a collar for holding the post of the holder. An inner tray of the packaging receives the collar such that the prosthesis is suspended within the inner tray. An outer tray lid receives the inner tray. An inner tray lid seals the inner tray and an outer tray lid seals the outer tray.

In U.S. Pat. No. 5,823,342, packaging for a heart valve device is disclosed that includes a container having an inner compartment. The container has an aortic orientation and a mitral orientation and is connected to be opened in either orientation. The packaging also includes an aortic support member located in the compartment that supports the heart valve device when the container is opened in the aortic orientation. The heart valve device is supported such that it is prepared for receiving a holding instrument for implantation as an aortic valve. The packaging further includes a mitral support member located in the compartment that supports the heart valve device when the container is opened in the mitral orientation. The heart valve device is supported such that it is prepared for receiving a holding instrument for implantation as a mitral valve.

Therefore, what is needed is a packaging container for a universal mechanical valve which preserves the universal nature of the packaging concept while shielding the valve from severe shock loading.

SUMMARY

One embodiment, accordingly, provides a universal packaging device which protects a fragile universal mechanical valve by isolating valve components from shock loads encountered during shipping and handling. To this end, a shock resistant packaging for a prosthetic heart valve includes a packaging container having a first member and a second member. A support shelf is mounted in the packaging container engaged with the first member for supporting a first side of a heart valve to be packaged in the container. An insert member is mounted in the packaging container engaged with the second member for supporting a second side of the heart valve to be packaged in the container.

A principal advantage of this embodiment is that the likelihood of damage during shipping and handling is significantly reduced.

BRIEF DESCRIPTION OF THE DRAWING FIGURES

DETAILED DESCRIPTION

Figure 1:
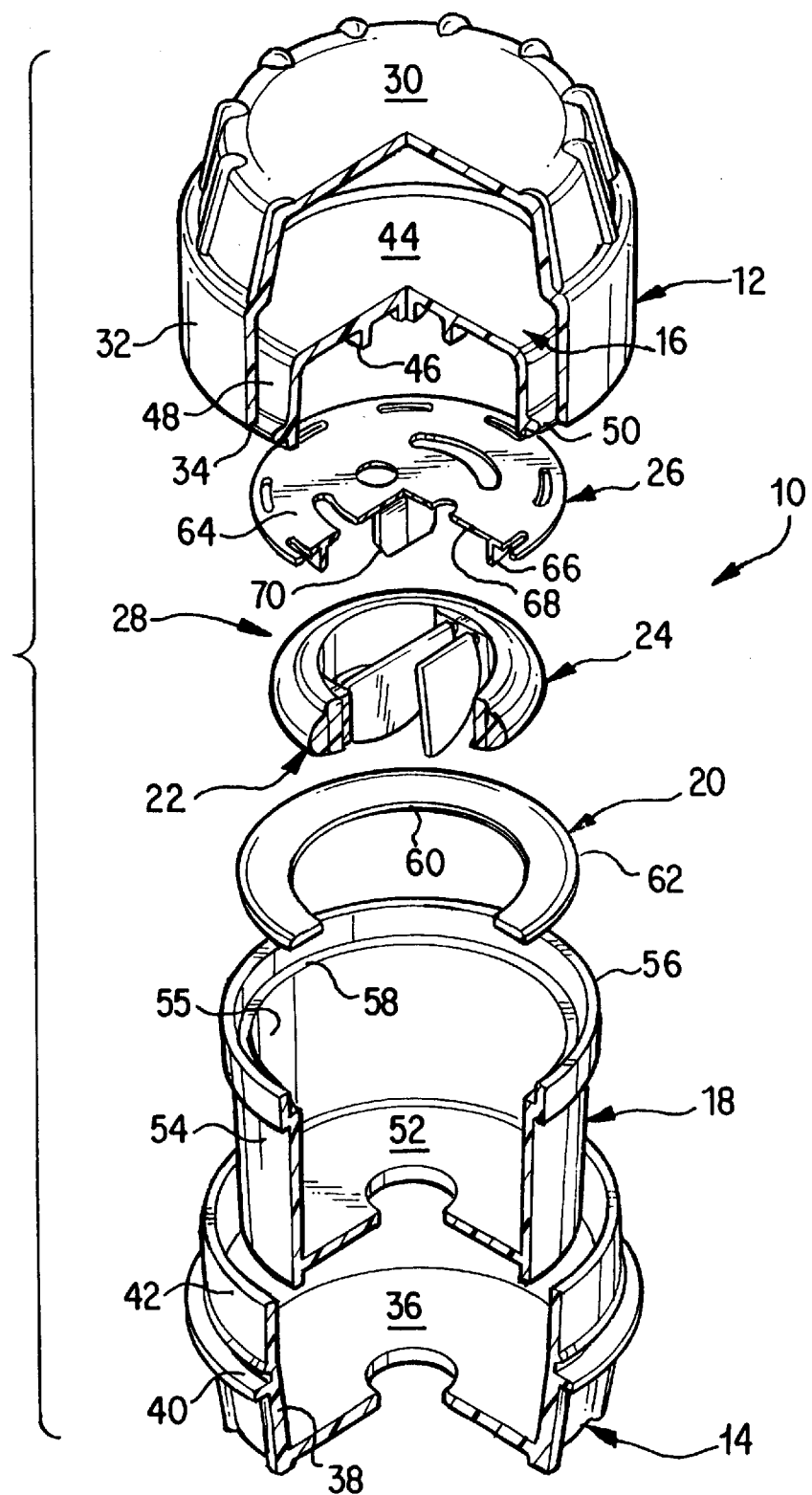
FIG. 1 is an exploded isometric view having a portion cut-away illustrating an embodiment of a packaging container.

A shock resistant packaging container 10 for a prosthetic heart valve 24, FIG. 1, includes an outer container having an outer top barrier 12 and an outer bottom barrier 14. An inner container includes an inner top barrier 16 and an inner bottom barrier 18 provided to nest inside the outer top and bottom barriers 12 and 14, respectively. A support shelf 20 is provided to be mounted in the inner bottom barrier 18 for supporting a first side 22 of the heart valve 24. An insert member 26 is mounted adjacent the inner top barrier 16 for supporting a second side 28 of the heart valve 24.

Outer top barrier 12 includes a planar surface 30 and an annular side wall 32 terminating in an annular rim 34. Outer bottom barrier 14 includes a planar surface 36 and an annular side wall 38 including an annular flange 40 on an outer surface 42 of side wall 38.

Inner top barrier 16 includes a planar surface 44 having an annular ring 46 extending therefrom, and an annular side wall 48 terminating in an annular flange 50. Inner bottom barrier 18 includes a planar surface 52 and an annular side wall 54 terminating in an annular rim 56. An annular lip 58 is formed on an inner surface 55 of side wall 54.

Figure 2:
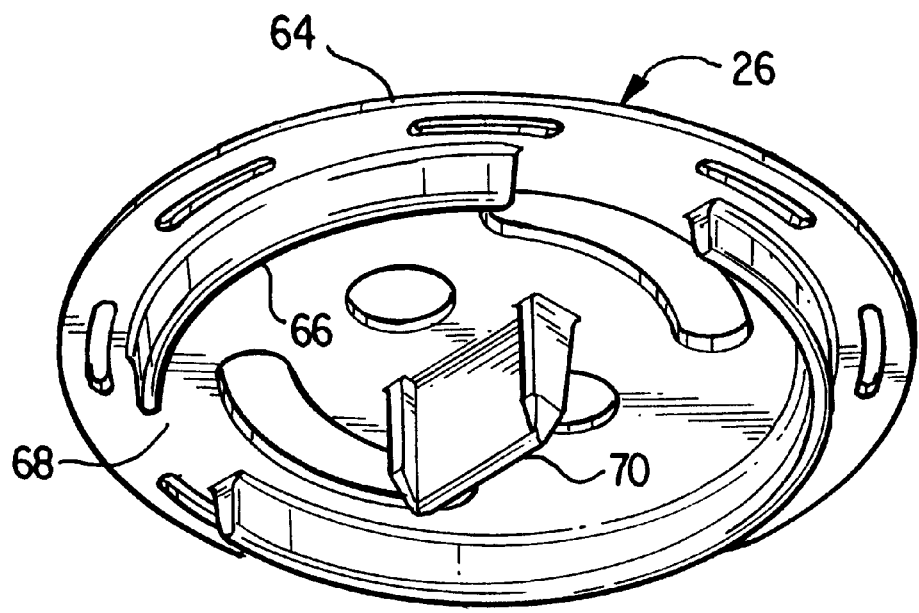
FIG. 2 is an isometric view illustrating an embodiment of an insert used in the packaging container.

Support shelf 20 includes a central annulus 60 and an annular peripheral surface 62. Insert member 26, includes planar disc 64 having an annular ring 66 extending from surface 68 of disc 64. The annular ring 66 may also be segmented as shown in FIG. 2. Ring 66 extends in a direction perpendicular to the surface 68 of disc 64. Insert member 26 also includes a wedge shaped tab 70 extending perpendicular from surface 68 of disc 64.

Figure 3:
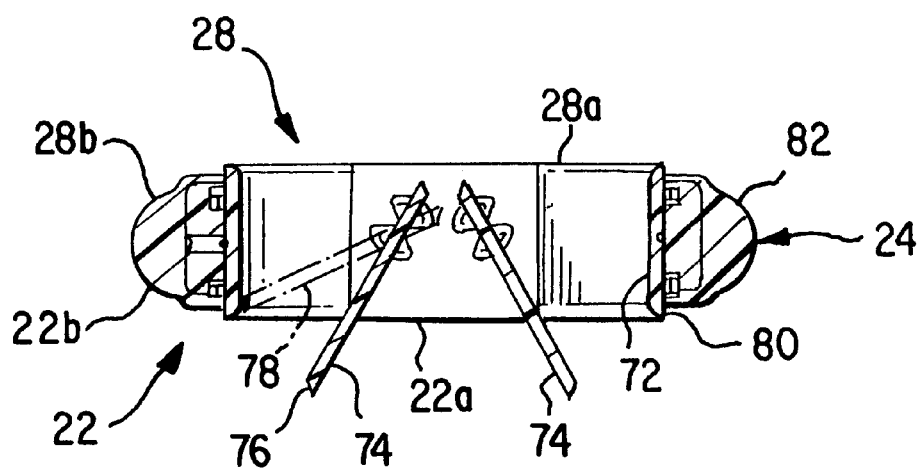
FIG. 3 is a cross-sectional side view illustrating an embodiment of a heart valve for storage in the packaging container.

Heart valve 24, FIG. 3, is formed by an orifice member 72 including at least one leaflet 74, each leaflet 74 being pivotally mounted therein for movement between a first open position 76 and a second closed position 78, illustrated in phantom outline. An outer surface 80 of orifice member 72 includes a sewing cuff 82 attached thereto. The first side 22 of valve 24 includes a surface 22a of orifice 72 and a surface 22b of sewing cuff 82. The second side 28 of valve 24 includes a surface 28a of orifice 72 and a surface 28b of sewing cuff 82.

Figure 4:
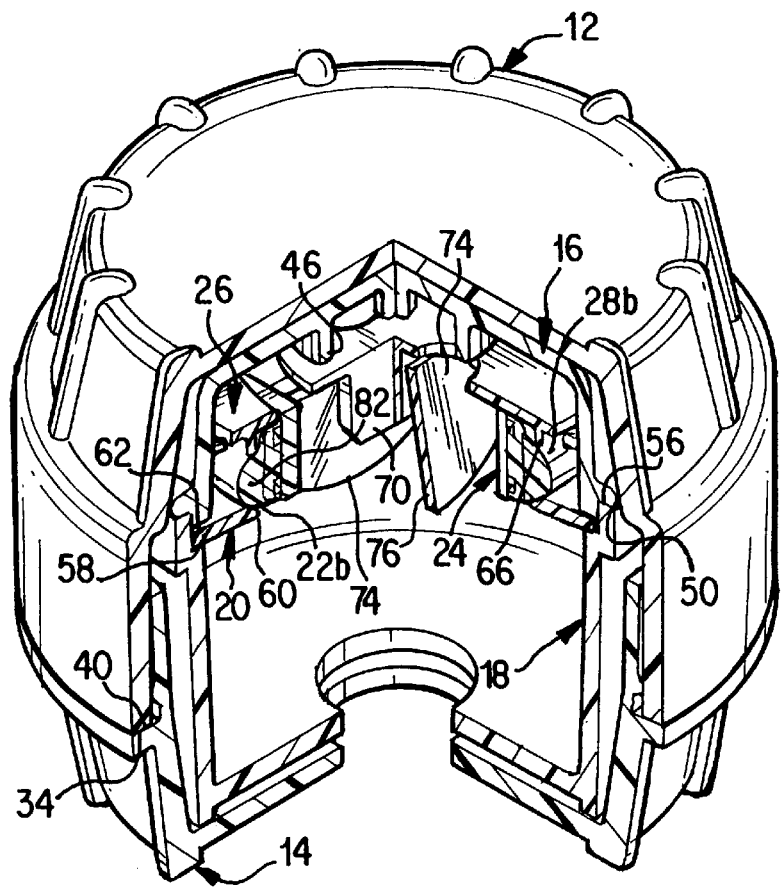
FIG. 4 is an isometric view having a portion cut-away illustrating an embodiment of the packaging container.

When the components are nested for packaging, FIG. 4, annular rim 34 of outer top barrier 12 engages flange 40 of outer bottom barrier 14. Annular rim 56 of inner bottom barrier 18 engages annular flange 50 of inner top barrier 16. Annular peripheral surface 62 of support shelf 20 seats on annular lip 58 of inner bottom barrier 18. Surface 22b of sewing cuff 82 of first side 22 seats on support shelf 20 at central annulus 60. Annular ring 66 of insert member 26 seats against surface 28b of sewing cuff 82 to restrain movement of heart valve 24. Wedge shaped tab 70 of insert member 26 seats between leaflets 74 of heart valve 24 and maintains the leaflets 74 in open position 76. Annular ring 46 of inner top barrier 16 limits movement of insert 26. Annular ring 66 of insert member 26 may be provided in various diameters to accommodate various size heart valves 24. The natural resiliency of the sewing cuff 82 reduces the amount of shock loading that is transmitted to the components of heart valve 24.

Figure 5:
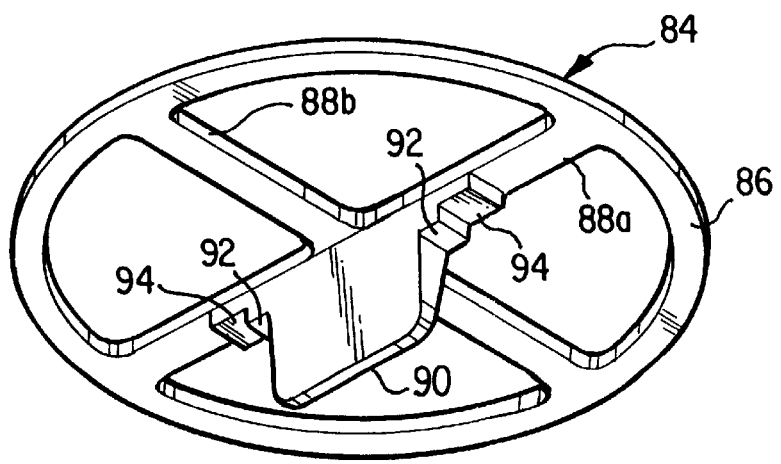
FIG. 5 is an isometric view illustrating another embodiment of an insert used in the packaging container.

In an alternative embodiment, FIG. 5, an insert member 84 includes an annular peripheral member 86, a first flexible cross member 88a and a second flexible cross member 88b, attached to the peripheral member 86. The first cross member 88a is perpendicular to the second cross member 88b. First cross member 88a includes a wedge shaped tab 90 extending therefrom. First cross member 88a also includes a plurality of steps 92 and 94 of varying height.

Figure 6:
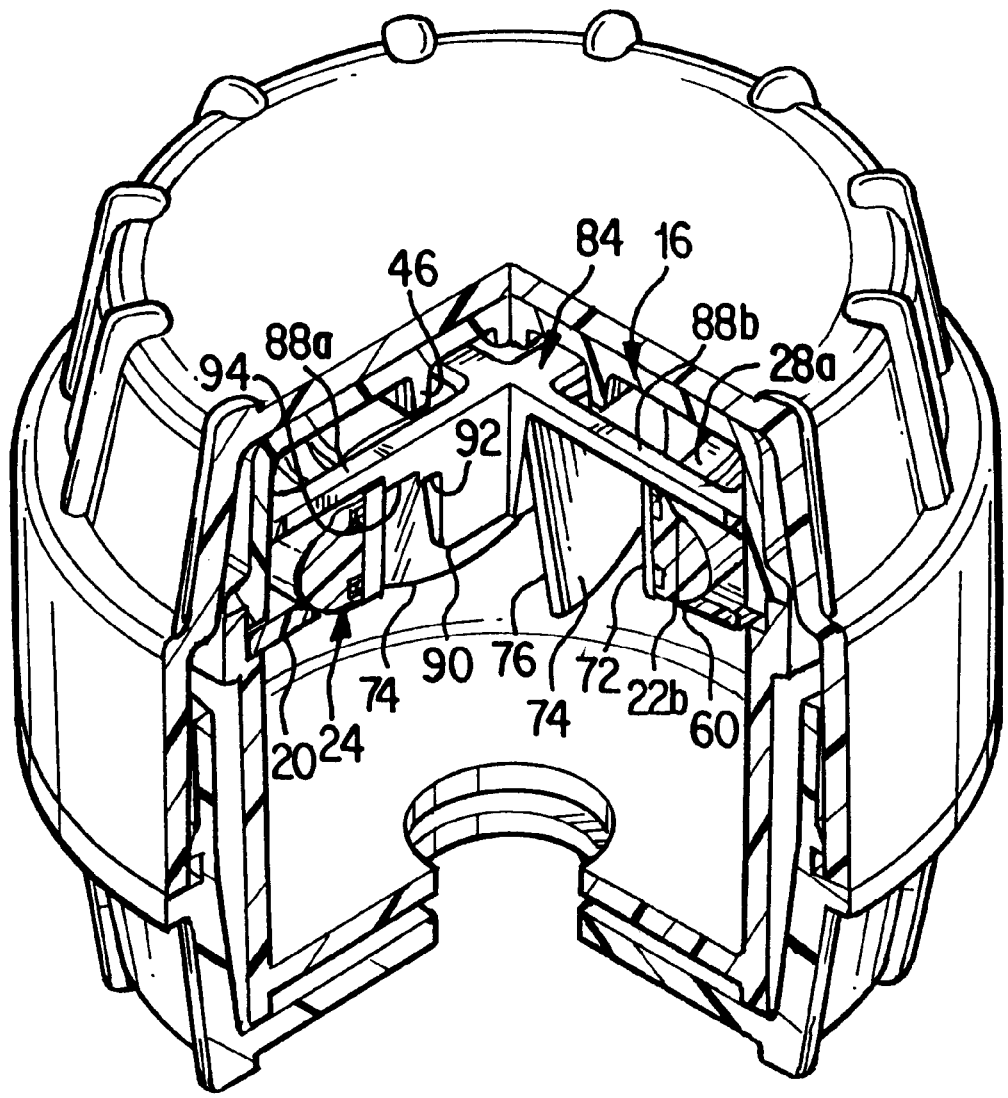
FIG. 6 is an isometric view having a portion cut-away illustrating another embodiment of the packaging container.

When the components are nested for packaging, FIG. 6, as described above, and insert member 84 is utilized in place of insert member 26, cross members 88a and 88b seat against surface 28a of orifice 72 to restrain movement of heart valve 24. Surface 22b of first side 22 seats on support shelf 20 at central annulus 60. Wedge shaped tab 90 of insert member 84 seats between leaflets 74 of heart valve 24 and maintains the leaflets 74 in open position 76. Annular ring 46 of inner top barrier 16 limits movement of insert member 84. Steps 92 and 94 of first cross member 84a are provided to accommodate various size heart valves 24. The natural resiliency of the sewing cuff 82 and the flexibility of cross members 88a and 88b, reduces the amount of shock loading that is transmitted to the components of heart valve 24.

As a result, one embodiment provides a shock resistant package for a prosthetic heart valve including a packaging container having a first member and a second member. A support shelf is mounted in the packaging container engaged with the first member for supporting a first side of a heart valve to be packaged in the container. An insert member is mounted in the packaging container engaged with the second member for supporting a second side of the heart valve to be packaged in the container.

Another embodiment provides a packaging container for a heart valve including a first member and a second member. A support shelf is mounted in the first member of the container. A heart valve has a first side and a second side, the first side being engaged with the support shelf. An insert member is engaged with the second side of the heart valve and is also engaged with the second member of the container.

A further embodiment provides a method of supporting a heart valve in a packaging container including forming a container having a first member and a second member. A support shelf is mounted in the first member of the container. A heart valve having a first side and a second side is mounted so that the first side is engaged with the support shelf. An insert member is mounted in engagement with the second side of the heart valve and also in engagement with the second member of the container.

As it can be seen, the principal advantages of these embodiments are that the packaging container protects fragile heart valve components by isolating them from the shock loads encountered during shipping and handling. This significantly reduces the likelihood of damage to the valve. The container preserves the universal nature of the packaging concept while shielding the valve from severe shock loading. The device can be adapted to other types of valves, both universal and position specific. The support scheme takes advantage of the natural resiliency of the fabric sewing cuff to reduce the amount of shock loading that could be transmitted to the valve components.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A heart valve packaging container system comprising:
 a container comprising a first barrier member and a second barrier member;
 a heart valve comprising an orifice member and a sewing cuff coupled to said orifice member, said sewing cuff having a first side and a second side;
 a support shelf coupled to the first barrier member, said support shelf contacting said heart valve solely at said sewing cuff; and
 an insert member coupled to the second barrier member and contacting said heart valve solely at said sewing cuff.

2. The container system as defined in claim 1 wherein the insert member includes a wedge shaped tab.

3. The container system as defined in claim 2 wherein the insert member includes an annular disc having a ring extending from a surface thereof, the annular ring engaging said second side of said sewing cuff.

4. The container system as defined in claim 3 wherein the annular ring extends generally perpendicular to the surface of the disc for engagement with the second side of the sewing cuff of said heart valve.

5. The container system as defined in claim 4 wherein the wedge shaped tab extends from the disc in a direction perpendicular to the surface of the disc for engaging and maintaining a pair of leaflets of the heart valve in an open position.

6. The container system as defined in claim 4 wherein the heart valve includes a sewing cuff, the support shelf engaging a first side of the sewing cuff and the annular ring engaging a second side of the sewing cuff.

7. The container system as defined in claim 3 wherein said annular ring is segmented.

8. The container system as defined in claim 1 wherein the insert member includes an annular disc having an annular ring extending from a surface thereof, the annular ring engaging said second side of said sewing cuff.

9. The container system as defined in claim 8 wherein the annular ring extends generally perpendicular to the surface of the disc for engagement with the second side of the sewing cuff of said heart valve.

10. The container system as defined in claim 9 wherein said annular ring is segmented.

11. A method of supporting a heart valve in a packaging container comprising the steps of:

providing a container including a first barrier member and a second barrier member;

coupling a support shelf to the first member of the container;

providing a heart valve having a sewing cuff comprising a first side and a second side;

coupling said support shelf to said first side of said sewing cuff;

providing an insert member coupled to said second side of said sewing cuff and to the second member of the container.

\* \* \* \* \*